US008103328B2

(12) United States Patent
Turner et al.

(10) Patent No.: US 8,103,328 B2
(45) Date of Patent: Jan. 24, 2012

(54) SELF-LOCATING SENSOR MOUNTING APPARATUS

(75) Inventors: Peter James Turner, San Diego, CA (US); Robert Matthews, San Diego, CA (US); Jamison Scott Woodward, Solana Beach, CA (US); Konstantine V. Ermolaev, San Diego, CA (US); Andrew D. Hibbs, La Jolla, CA (US)

(73) Assignee: Quantum Applied Science and Research, Inc., San Diego, CA (US)

( * ) Notice: Subject to any disclaimer, the term of this patent is extended or adjusted under 35 U.S.C. 154(b) by 655 days.

(21) Appl. No.: 12/243,461

(22) Filed: Oct. 1, 2008

(65) Prior Publication Data

US 2009/0088619 A1    Apr. 2, 2009

Related U.S. Application Data

(60) Provisional application No. 60/960,472, filed on Oct. 1, 2007.

(51) Int. Cl.
*A61B 5/0478* (2006.01)
*A61B 19/00* (2006.01)

(52) U.S. Cl. ......... 600/383; 600/544; 600/553; 600/587

(58) Field of Classification Search .................. 600/383, 600/386, 390, 393, 544, 545, 553, 587; 2/209.13; 73/12.01, 12.09
See application file for complete search history.

(56) References Cited

U.S. PATENT DOCUMENTS

| | | | |
|---|---|---|---|
| 3,508,541 A | 4/1970 | Westbrook et al. | |
| 3,998,213 A | 12/1976 | Price | |
| 4,709,702 A * | 12/1987 | Sherwin | 600/383 |
| 4,967,038 A | 10/1990 | Gevins et al. | |
| 5,038,782 A | 8/1991 | Gevins et al. | |
| 5,348,006 A * | 9/1994 | Tucker | 600/383 |
| 5,357,957 A | 10/1994 | Itil et al. | |
| 5,479,934 A | 1/1996 | Imran | |
| 5,800,351 A | 9/1998 | Mann | |
| 5,914,661 A | 6/1999 | Gross | |
| 6,161,030 A | 12/2000 | Levendowski et al. | |
| 6,167,298 A | 12/2000 | Levin | |
| 6,381,481 B1 | 4/2002 | Levendowski et al. | |
| 6,640,122 B2 | 10/2003 | Manoli et al. | |
| 6,691,324 B1 | 2/2004 | Nakamura | |
| 6,708,051 B1 | 3/2004 | Durousseau | |
| 7,158,822 B2 | 1/2007 | Payne, Jr. | |

(Continued)

FOREIGN PATENT DOCUMENTS

WO    WO 2008067839 A1 *    6/2008

*Primary Examiner* — Lee Cohen
*Assistant Examiner* — Erin M Cardinal
(74) *Attorney, Agent, or Firm* — Diederiks & Whitelaw, PLC

(57) ABSTRACT

A self-locating mounting apparatus for holding objects such as sensors at specific positions on a subject's head includes a central mount constituted by a plurality of inextensible elements adapted to fit over the top of a subject's head. In addition, the mounting apparatus includes an adjustable circumferential band adapted to circle the subject's head and connect the central mount to inextensible side elements via sliding joints. A plurality of biasing elements provide a force for biasing sensor mounting units on the mounting apparatus against a subject's head, allowing for long-term sensing while minimizing interference forces on the mounting units. Advantageously, the mounting apparatus holds sensors within approximately 5 mm of their desired measurement positions over a range of subject head sizes.

25 Claims, 8 Drawing Sheets

U.S. PATENT DOCUMENTS

| | | |
|---|---|---|
| 2002/0029005 A1 | 3/2002 | Levendowski et al. |
| 2005/0107716 A1* | 5/2005 | Eaton et al. .................. 600/544 |
| 2005/0266967 A1* | 12/2005 | Considine et al. ............. 482/84 |
| 2005/0277821 A1 | 12/2005 | Payne, Jr. |
| 2006/0038694 A1* | 2/2006 | Naunheim et al. ............ 340/665 |
| 2006/0189852 A1 | 8/2006 | Greenwald et al. |
| 2007/0093706 A1 | 4/2007 | Gevins et al. |
| 2007/0106169 A1* | 5/2007 | Fadem .......................... 600/544 |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0255127 A1 | 11/2007 | Mintz et al. |
| 2008/0294031 A1* | 11/2008 | Wilson et al. ................. 600/383 |
| 2010/0198042 A1* | 8/2010 | Popescu et al. ............... 600/383 |
| 2010/0274153 A1* | 10/2010 | Tucker et al. ................. 600/544 |

* cited by examiner

SELF-LOCATING SENSOR MOUNTING APPARATUS

CROSS-REFERENCE TO RELATED APPLICATIONS

The present application claims the benefit of U.S. Provisional Patent Application Ser. No. 60/960,472 entitled "Self Locating Mounting apparatus for Holding Objects on the Head" filed Oct. 1, 2007.

STATEMENT REGARDING FEDERALLY SPONSORED RESEARCH AND DEVELOPMENT

This invention was made with Government support under Contract No. W91ZLK-04-P-0235 awarded by NAVAIR. The Government has certain rights in the invention.

BACKGROUND OF THE INVENTION

1. Field of the Invention

The present invention pertains to the art of sensing devices and, more particularly, to a self-locating mounting apparatus in the form of headgear for accurately positioning sensors on a subject, such as for medical purposes.

2. Discussion of the Prior Art

There are a number of applications in which it is necessary to place sensors on the scalp of a human subject at defined locations relative to the head. One principle application is in the recording of electrical brain activity via an array of discrete bioelectrodes or electroencephalography (EEG) sensors that measure the scalp surface potential at specific locations. The standard set of measurement locations is known as the International 10/20 electrode placement scheme and is defined based on linear ratios tied to specific physiological markers, such as the nasion (intersection of the frontal and two nasal bones, of the human skull), the inion (the most prominent projection of the occipital bone at the lower rear part of the skull), and the pre-auricular points (adjacent the ears). More recently, subsets of sensor positions have been defined to be used in measurement of specific cognitive states, e.g., cognitive overload. In this case, sensors can be infrared sensors to detect brain blood oxygen content or biopotential electrodes. Other sensors, such as accelerometers and/or impact sensors, can be placed at specific locations on the head to quantify forces on the head resulting from collisions and explosions that could lead to brain trauma.

Existing methods to position sensors and other objects on the head of a subject involve careful measurements by trained personnel. Measurement reference points such as the nasion are used first to define starting points for measurement of head circumference and the distance from the front to the back of the head across the centerline. Desired positions are then defined via fraction distances along these key measurement lines or along lines that connect points on the key measurement lines. The technical challenge is that the size and shape of the human head can vary significantly. For example, the circumference along the nasion and inion points typically varies by 8 cm in adults and the distance across the top of the head typically varies by 4 cm front to back. The simplest solution that has been tried is to hold sensors in an entirely elasticized structure that can expand in all directions, such as a latex cap. See, for example, the prior art arrangement depicted in FIG. 1 herein, showing a stretchable (elastic) cloth hat body 2 including electrodes 4. One such cap is taught in U.S. Pat. No. 4,967,038 entitled "Dry Electrode Brain Wave Recording System" filed Aug. 25, 1989, which is incorporated herein by reference.

When working with sensor arrangements adapted to fit multiple head sizes, the change in head dimension is ideally divided equally across all the sensor positions, resulting in an equal relative expansion of the distance between sensors. However, in practice, expandable mounting apparatuses such as hat body 2 shown in FIG. 1 become caught on parts of the head and the expansion is uneven. In addition, sensors in mounting apparatuses which are entirely elasticized are prone to become tilted, i.e., they do not sit flat against the head, due to the dragging force generated when the structure is put on. The problem of tilting is increased when the objects require application of a force normal to the head. In this case, it is better to attach the sensors or objects to the mounting apparatus via their outer surface (with respect to the scalp) so as to produce a component of the force in the direction normal to the head. However, attaching the objects in a plane at a considerable distance off the scalp increases the moment that acts to rotate the objects in direction proportion to distance.

Accordingly, there exists a need for a mounting apparatus to hold objects such as sensors against the scalp wherein the apparatus expands when placed on a subject's head in order to fit varying head sizes, but which effectively locates the sensors at a desired position relative to the head and prevents rotation of objects when the mounting apparatus is in use.

SUMMARY OF THE INVENTION

The present invention is directed to a self-locating mounting apparatus in the form of headgear for accurately positioning objects such as sensors against a subject's head. The mounting apparatus includes a central mount having a plurality of inextensible elements extending therefrom, and an inextensible circumferential band connected by sliding expanding joints to the central mount via inextensible side elements. In use, the sliding joints are employed to position the circumferential band relative to the central mount in order to automatically fit the mounting apparatus to a variety of subject head sizes. Adjustment means on the circumferential band can also be utilized to customize the mounting apparatus to a particular subject. Mounting units adapted to retain objects such as electrodes and the like are connected to the mounting apparatus, and biasing elements in the form of elastic cords or springs are utilized to bias the mounting units towards the subject. Communication and power wires connect electrodes in the mounting apparatus to a control apparatus and power source. The mounting apparatus may also include a data filter/digitizer and a wireless link for communicating data from the sensors to a remote location. In accordance with a preferred embodiment of the present invention, the mounting apparatus is adapted to hold an array of EEG electrodes against the scalp of a subject in accordance with the international 10/20 electrode placement scheme. In accordance with another preferred embodiment, mounting apparatus is a self-contained unit adapted for use with helmets, such as military helmets.

With this construction, the present invention allows for accurate placement of sensors or other objects by a person with no specific training or skill, and eliminates the need for careful measurements of an individual subject's head. The advantages of the present invention lend itself to a variety of applications, such as medical diagnostics and monitoring of military personnel. Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
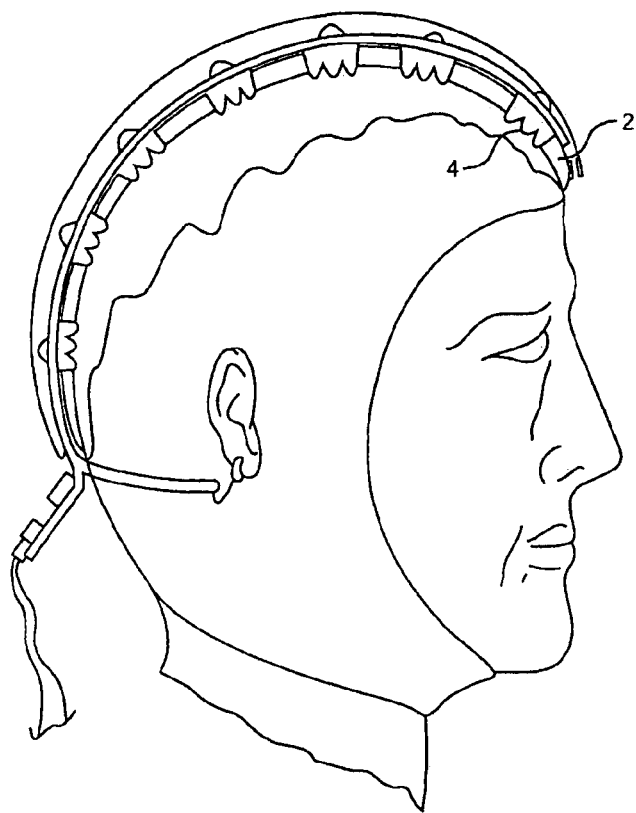
FIG. 1 illustrates a prior art sensing system utilizing a stretchable cloth hat including electrodes.
Figure 3:
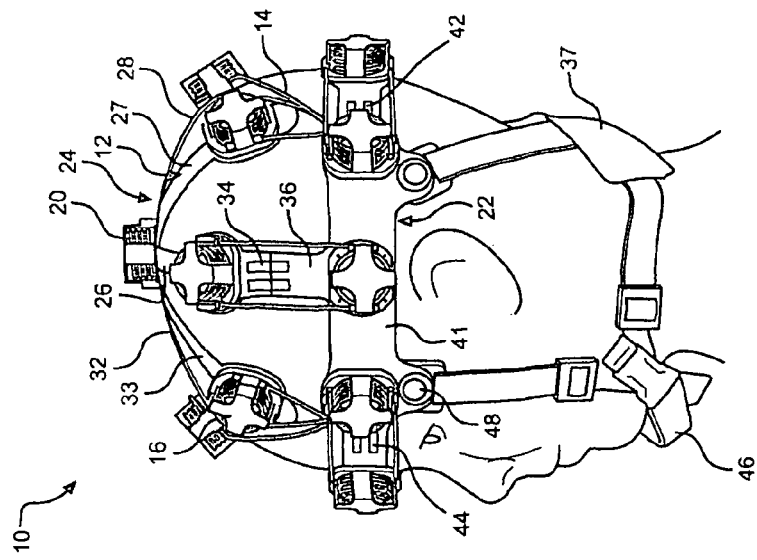
FIG. 3 is a side perspective view of the mounting apparatus of FIG. 2.
Figure 2:
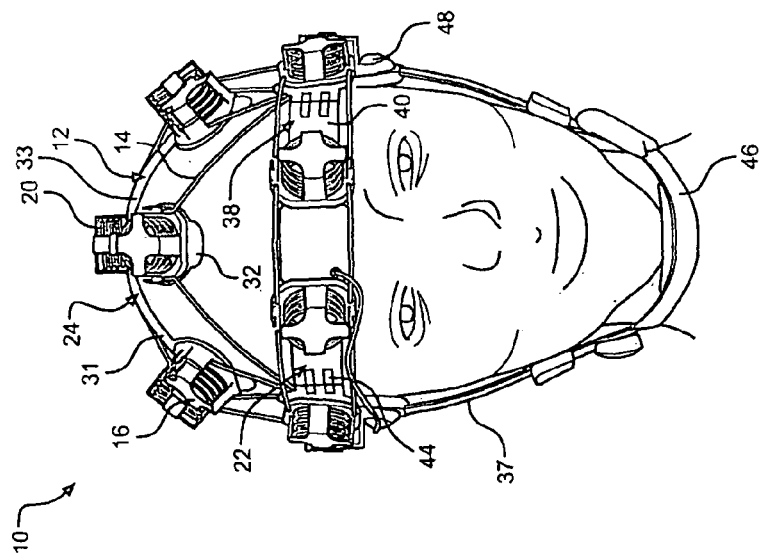
FIG. 2 is a front perspective view of a mounting apparatus in accordance with the present invention including a chin strap retaining member.
Figure 5:
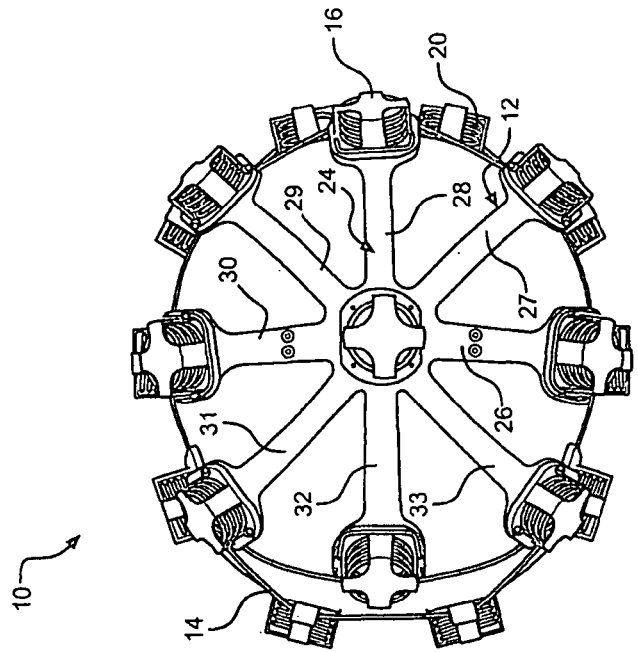
FIG. 5 is a top perspective view of the mounting apparatus of FIG. 2.
Figure 4:
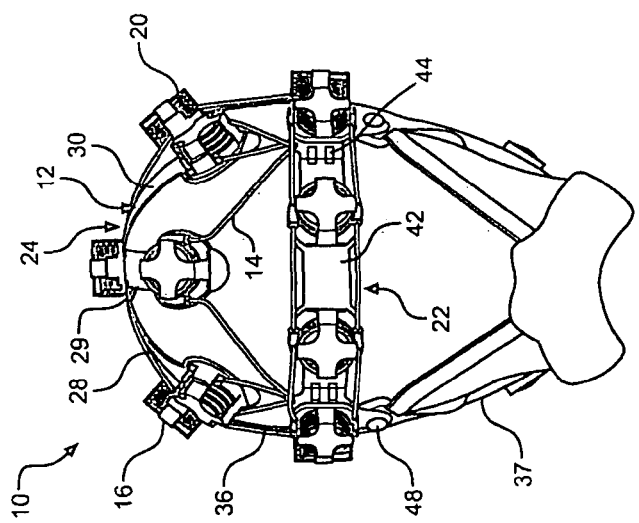
FIG. 4 is a back perspective view of the mounting apparatus of FIG. 2.

With initial reference to FIG. 2, a first embodiment of the mounting apparatus of the present invention is indicated at 10. In general, mounting apparatus 10 is in the form of headgear including numerous non-elastic inextensible elements or bands, generally indicated at 12, and tensioning or biasing elements 14 in the form of elastic cords. It should be understood that the term inextensible means that bands 12 are incapable of being stretched during regular use. In the first embodiment shown, bands 12 are flexible plastic bands. A plurality of mounting units or pods 16 are connected at various points to bands 12 and are utilized for holding an array of sensors or other objects against the scalp of a subject. In a preferred embodiment, pods 16 include springs 20 which provide a controlled force to bias biopotential sensors or EEG electrodes 18 (such as those depicted in FIGS. 8 and 9) housed within pods 16 against a subject's scalp in accordance with the international 10/20 electrode configuration for electroencephalography (EEG) placement. An example of EEG electrodes contemplated for use with the present invention and particularly suited to function in the presence of hair, are described in U.S. patent application Ser. No. 12/153,659, incorporated herein by reference. a2

The specific configuration of mounting apparatus 10 will now be discussed with reference to FIGS. 2-6. Principle elements of mounting apparatus 10 include an adjustable circumferential band 22 that fits around the widest part of a subject's head (i.e. from the forehead to the back, just over the ears) in a manner similar to a regular baseball cap or hat, and a central mount or petal element 24 that sits on top of the head. Petal element 24 includes bands 12, shown as eight non-elastic inextensible elements 26-33 (best seen in FIG. 5), and is connected to circumferential band 22 via sliding expansion joints 34 at the approximate midpoint of opposing side band elements 36. Preferably, circumferential band 22 includes an adjustment means or mechanism 38. In the embodiment shown, adjustment means 38 is constituted by four inextensible band segments 40-43 interconnected by sliding expansion joints 44, with the sliding joints 44 approximately centered between the four cardinal points of the head, i.e., the nose, (nasion), the two ears, and the spine (inion). Sliding expansion joints 34 and 44 allow for adjustment of petal element 24 on the head such that petal element 24 can be properly located at the midpoint between the front and back of the head for a variety of head sizes. With this configuration, inextensible elements 26 and 30 are held against a subject by respective opposing side band elements 36, while the remaining inextensible elements 27-29 and 31-33 are pulled against the head by biasing elements 14 without the constraint of sliding joints 34 or 44. When positioned on a subject's head as shown, biasing elements 14 and springs 20 of pods 16 force sensors 18 against the subject's head. In order to counter this force, a retaining member, preferably in the form of a chin strap assembly 46, is utilized. In the preferred embodiment shown, chin strap assembly 46, which is used in combination with a side and neck strap assembly 37 (see FIGS. 2-4) to secure apparatus 10 on the subject's head, connects to circumferential band 22 at four connecting points indicated at 48.

Figure 6:
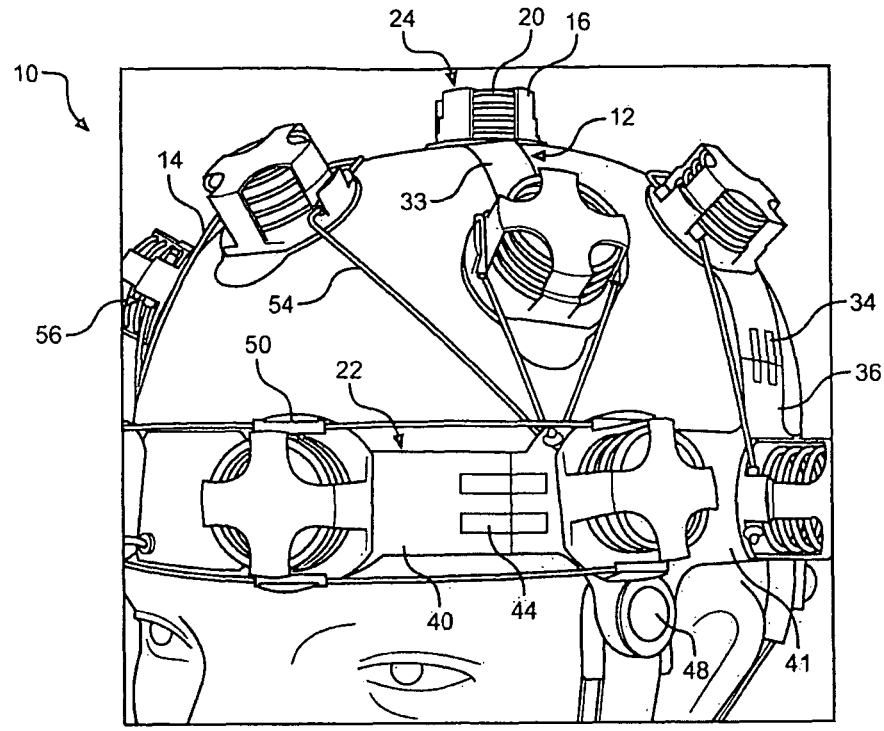
FIG. 6 is a partial close-up view of the mounting apparatus of FIG. 2.

FIG. 6 depicts a close-up view of one sliding expansion joint 34 connecting one of the opposing side band segments 36 to circumferential band 22, as well as one of the sliding joints 44 in circumferential band 22. In use, forces applied by biasing elements 14 contract elements of mounting apparatus 10. More specifically, petal element 24 and bands 12 slide freely with respect to one another through the use of sliding expansion joints 34 and segments 40-43 are free to slide past one another at sliding joints 44, such that mounting apparatus 10 can expand or contract as necessary to fit a particular head size, with biasing elements 14 also providing the force necessary to bias pods 16 against a subject's head. With this configuration, the sliding expansion joints 34 of mounting apparatus 10 allows for one-dimensional extension parallel to the longitudinal axis of inextensible bands 12 while resisting rotation away from and twisting about the longitudinal axis.

Preferably, sliding expansion joints 44 of circumferential band 22 allow in the order of ±0.5-1.0 cm of extension between them, thus allowing a total circumferential bead size range of approximately ±2 cm about the nominal band size of the system. Such a range of extension is adequate to fit approximately 70% of adults. Individuals outside this range can be fitted by small and large versions of mounting apparatus 10, centered on band sizes 3-4 cm less and 3-4 cm larger, respectively. However, it should be noted that although a range of three system band sizes has been selected, the invention is not limited to such, and any desired size range may be utilized in accordance with the present invention. In general, more size ranges increases the positioning accuracy across an array of electrodes 18. In order to meet the electrode position accuracy required in a standard 10/20 sensor arrangement, three sizes, each covering a band size range of 6 cm, is adequate. In some applications, such as some cognitive state monitoring, the requirement of absolute electrode positioning is relaxed and two sizes, or even one size, are/is adequate.

With respect to the connection between petal element 24 and circumferential band 22, the distance across the top of the head along the center line from the nasion to the inion varies between individuals. When mounting apparatus 10 is utilized for EEG, sliding expansion joints 44 preferably provide a range of expansion of approximately ±1 cm in order to provide the accuracy needed for positioning electrodes 18. Individuals outside of this range can be accommodated by a discrete smaller or larger size (i.e., length) of elements 26-33. It should be understood that inextensible elements 26-33 of arms 12 function to hold electrodes 18 or other objects in the correct angular orientation with respect to each other. This occurs naturally by the angle elements 26-33 make to the petal axis, and is unaffected by changes in the length of elements 26-33.

It should be noted that the requirement for absolute position accuracy relative to head fiducial marker points (i.e., points of reference) in a sensor array mounting system is different from the positional reproducibility of the mounting system. The latter instance refers to the run-to-run variations in electrode position each time the sensor array is put on. Advantageously, the present mounting apparatus 10 allows for reproducibility independent of the variation of absolute electrode position with subject head size.

The manner in which mounting apparatus 10 is automatically fit to an individual subject will now be discussed with reference to FIG. 6. As previously noted, tension between elements of mounting apparatus 10, including pods 16, is provided by biasing elements 14. More specifically, each pod 16 includes opposing side guides 50 through which an elastic cord 54 of one of biasing elements 14 is threaded. In order to provide a comfortable fit, tension force provided by biasing elements 14 is approximately constant over the range of intended subject head sizes. This is accomplished by making the length of each: biasing element 14 as long as reasonably possible. Thus, rather than connect biasing elements 14 at the inside of a pod 16, elastic cords 54 are passed through a smooth guide, such as a TEFLON tube 56, and tied off at the end of tube 56. Tube 56 adds an extra length in the order of 2 cm to elastic cord 54, thereby reducing the fractional extension placed on elastic cord 54 by the expansion of mounting apparatus 10 needed to accommodate the desired range of head sizes.

Figure 7:
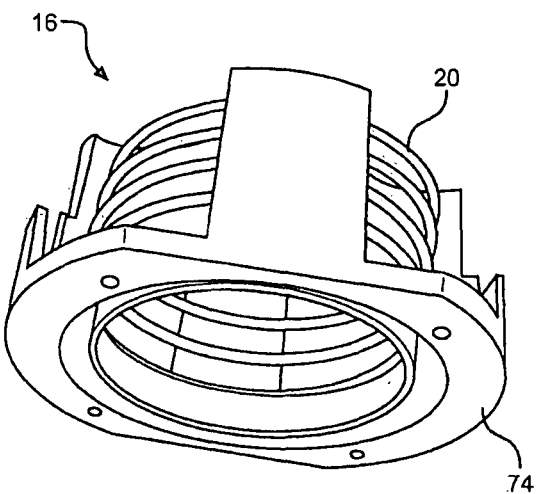
FIG. 7 is a perspective view of a sensor mounting unit for use with the present invention.
Figure 8:
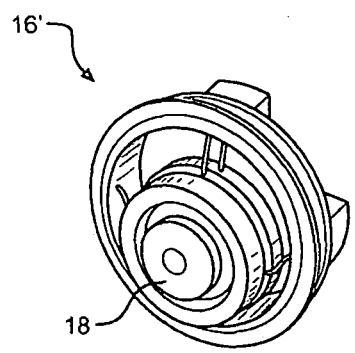
FIG. 8 is a perspective view of a sensor loosely mounted in an alternative mounting unit.
Figure 9:
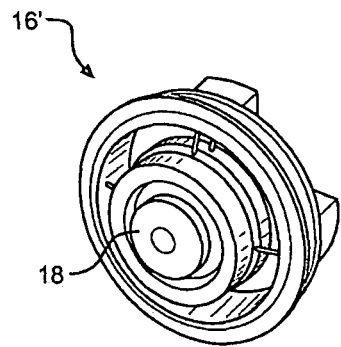
FIG. 9 is a perspective view of a sensor captured in the center of the mounting unit of FIG. 8.

As previously noted, mounting apparatus 10 is preferably utilized in conjunction with EEG electrodes 18, depicted in FIGS. 8 and 9. An enlarged view of a preferred embodiment of pod 16 suitable for holding one of EEG electrodes 18 is depicted in FIG. 7. In use, a base 74 of each of the pods 16 rests against a subject's head. The height of pod 16 and the properties of spring 20 set a controlled biasing force that holds electrode 18 against the subject. Spring 20 has the further benefit that it maintains electrode 18 comfortably against a subject's head even if mounting apparatus 10 is momentarily pulled away from the head by a small displacement force.

A method of mounting objects such as EEG electrode 18 within pod 16 will now be described with reference to FIGS. 8 and 9 depicting an alternative pod 16' for housing one of electrodes 18. When electrode 18 is mounted in pod 16' such that electrode 18 can move laterally within pod 16', a potential problem is created in that electrode 18 can be pulled to the limit of its travel when mounting apparatus 10 is put on and remain pressed against a side of pod 16', thereby reducing the desired isolation to lateral motion. This circumstance is illustrated in FIG. 8. To minimize such events, pod 16' contains open spaces that allow objects within to be re-centered manually. In practice, this re-centering involves wiggling electrode 18 in order to free it to return to the center of its travel. Although easy to do, this approach requires addressing each electrode 18 individually. In a preferred embodiment for use with the present invention, electrodes 18 are fixed in the center of respective pods 16' before mounting apparatus 10 is fit to a subject's head then, after mounting apparatus 10 is properly positioned, are released to have a normal range of travel within respective pods 16'. In one embodiment, a set of tensioning cables constituted by nylon lines (not labeled) are utilized in locating EEG electrode 18 in the center of pod 16' as depicted in FIG. 9.

Figure 10:
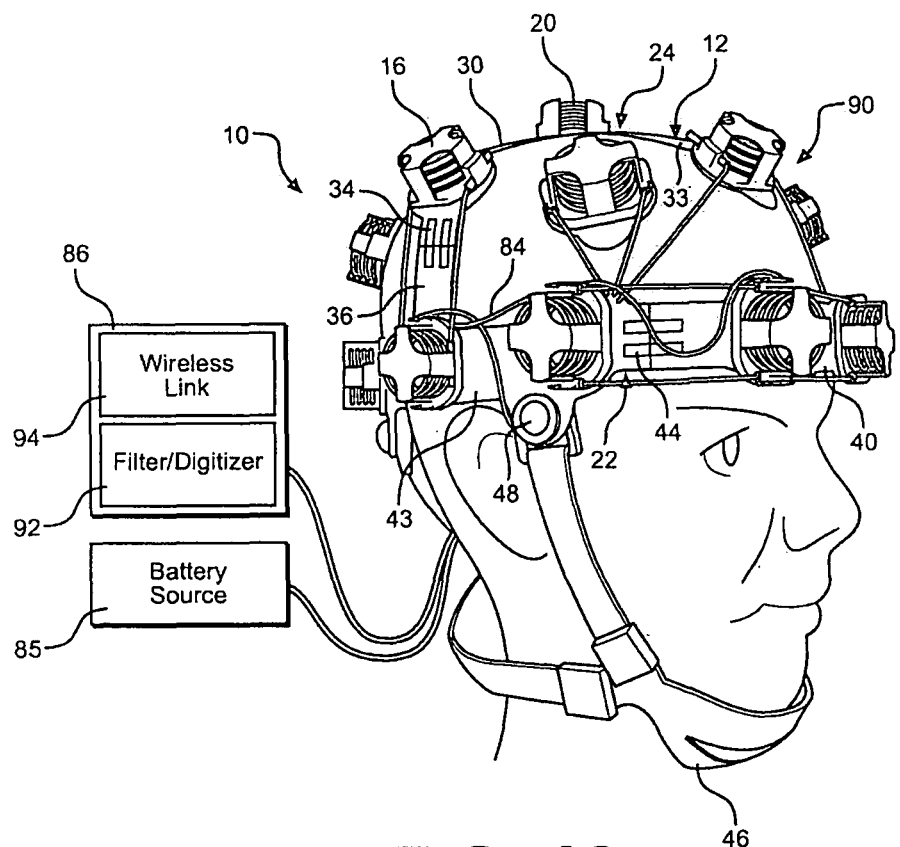
FIG. 10 is a perspective view of a mounting apparatus of the present invention including a full sensor array connected to a controller and battery source.

With reference to FIG. 10, a complete mounting apparatus 10 is illustrated to include a plurality of electrodes configured in a 10/20 arrangement. Communication and power Wires 84 connect the electrodes (not shown) housed in pods 16 to a power source such as a battery 85 and to a control apparatus 86. If desired, mounting apparatus 10 can hold other system components as needed. For example, a complete mounting apparatus 10 may comprise an upper petal-based array of seven sensors generally indicated at 90, two ground reference sensors (not shown), a unit 92 to filter and digitize the data, battery unit 85 and a wireless link 94 to telemeter data from mounting apparatus 10 to a remote location.

Advantageously, the present invention allows for sliding joints 34 and 44 to expand in such a way as to hold sensors within, preferably, ±5 mm of their desired measurement position for a defined range of subject head sizes. As previously discussed, electrodes 18 are connected to bands 12 via pods 16, 16' which allows electrodes 18 to move tangentially to the scalp of a subject by several millimeters, and to be held against the scalp of a subject independently to provide a high degree of mechanical isolation from local movement of the scalp, such as is caused by facial expressions, and to inertial forces acting on pods 16, 16'. The structure of mounting apparatus 10 also allows for placement of the system on a subject's head by an unskilled person, and allows the system to be worn for extended periods of time with minimal discomfort to the subject.

Figure 11:
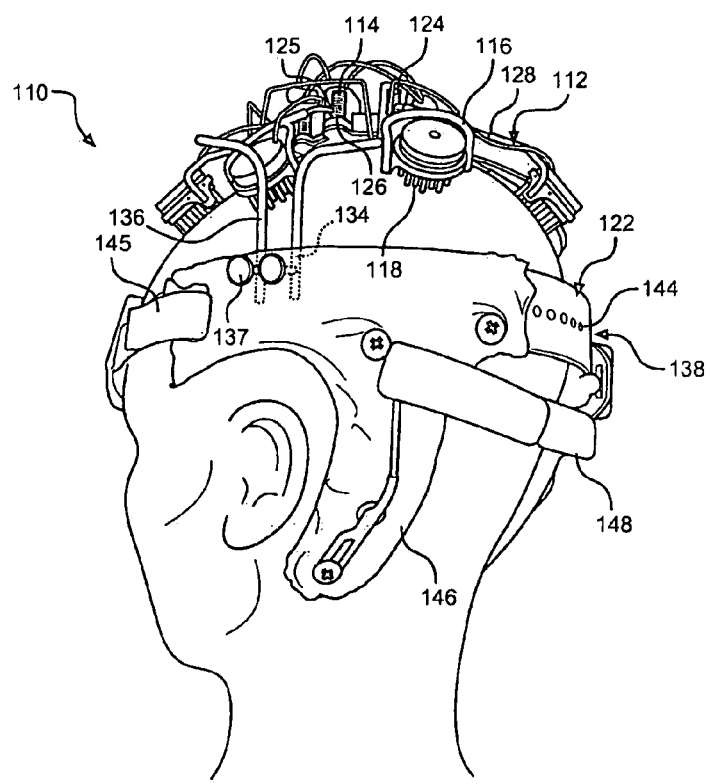
FIG. 11 is a rear perspective view of a second mounting apparatus of the present invention.
Figure 12:
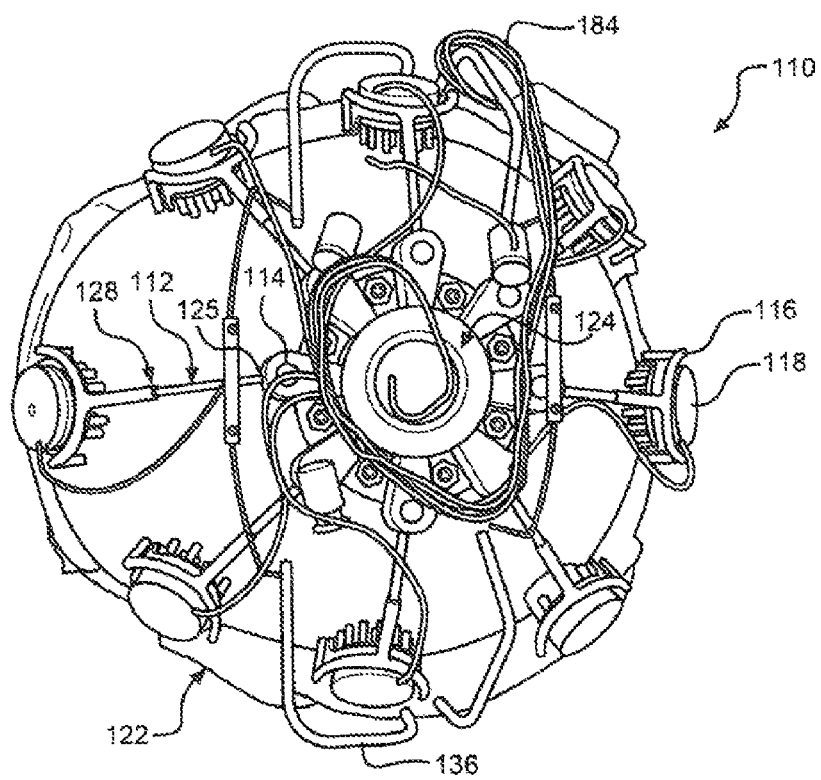
FIG. 12 is a top view of the mounting apparatus of FIG. 11.

A second embodiment of the present invention will now be discussed with reference to FIGS. 11 and 12 wherein a mounting apparatus 110 is depicted including eight non-elastic inextensible elements or cantilevered arms 112 and biasing elements in the form of spring assemblies 114, which bias arms 112 towards a subject's head. A plurality of mounting units 116 are connected to arms 112 and are adapted to house sensors or other objects, preferably EEG electrodes 118. Principle elements of mounting apparatus 110 include a circumferential band 122 that fits around the widest part of a subject's head, and a petal is element or central mount 124 that sits on top of the head. Unlike the flexible bands 12 in the first embodiment, arms 112 are rigid and are attached to central mount 124 via rotating joints 125.

In use, arms 112 are biased against a subject's head via spring assemblies 114 built into central mount 124. Spring assemblies 114 can incorporate rigid stops 126 so that arms 112 are limited in their maximum rotation with respect to central mount 124 in order to facilitate placement of mounting apparatus 110 on a subject's head. In a preferred embodiment, arms 112 of mounting apparatus 110 include telescoping mechanisms 128 which only allow arms 112 to slightly expand or contract in accordance with natural movements in a subject's scalp, such as caused by changes in facial expressions. Such structure results in greater comfort, without loss of sensor positioning accuracy. In addition, central mount 124 is connected to circumferential band 122 via adjustable connecting points or sliding joints 134, which are generally centered above the ears of a subject's head. More specifically, pairs of opposing inextensible side arm elements 136 connect central mount 124 to circumferential band 122 at sliding joints 134. In the embodiment shown, adjustable clamping screws 137 are utilized to retain side arm elements 136 at the desired location with respect to circumferential band 122.

Circumferential band 122 preferably includes one or more adjustment mechanism means 138. In the embodiment depicted in FIG. 11, adjustment means 138 in the form of an adjustable band 144 and a plurality of VELCRO straps indicated at 145. When mounting apparatus 110 is positioned on a subject's head as shown, spring assemblies 114 bias mounting units 116 and associated electrodes 118 against a subject's head, providing an upward force against the subject. In order to counter this force, a retaining member in the form of a padded retaining arm assembly 146 is provided. Retaining arm assembly 146 is adapted to be positioned behind the ears of a subject in order to provide a downward force to mounting apparatus 110 and preferably includes an adjustable rear band 148 to allow for further customization of mounting apparatus 110. A plurality of communication and power wires 184 connect electrodes 118 to a control apparatus and battery source in the same manner as discussed with reference to mounting apparatus 10. As with the first embodiment of the present invention, it should be understood that mounting apparatus 110 allows for placement of a sensing array on a subject's head by an unskilled person, and allows the array to be worn for extended periods of time with minimal discomfort to the subject.

Figure 13:
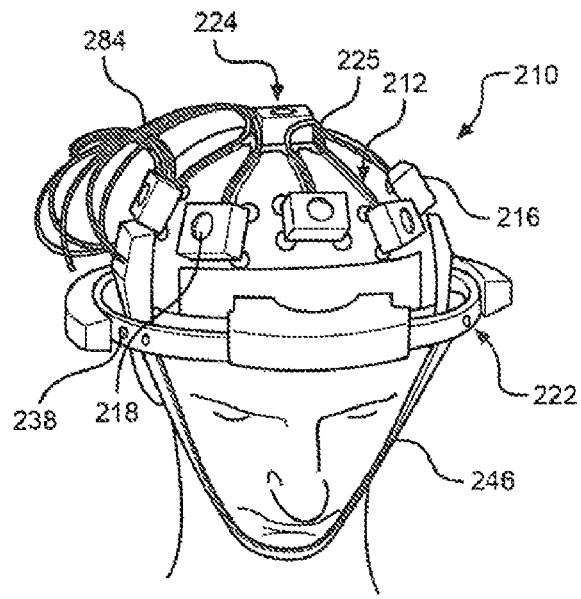
FIG. 13 is a front perspective view of a third mounting apparatus of the present invention.
Figure 14:
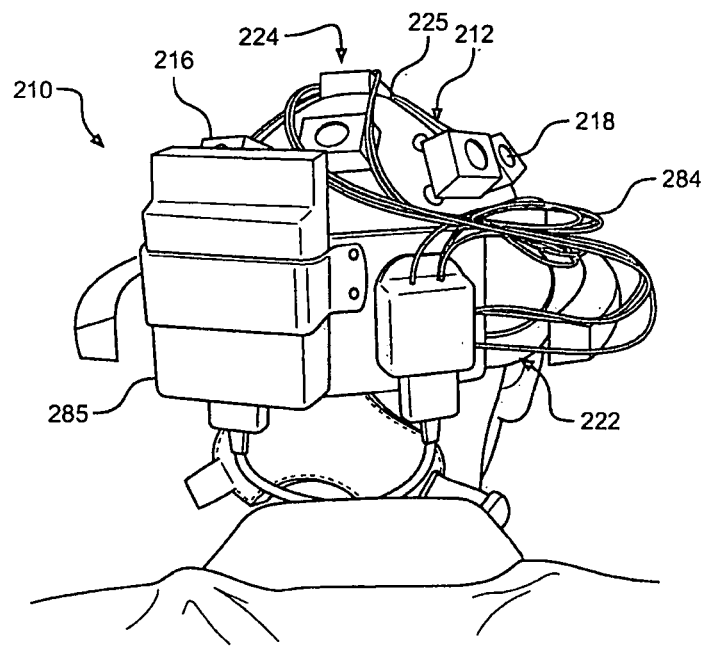
FIG. 14 is a rear perspective view of the mounting apparatus of FIG. 13.
Figure 15:
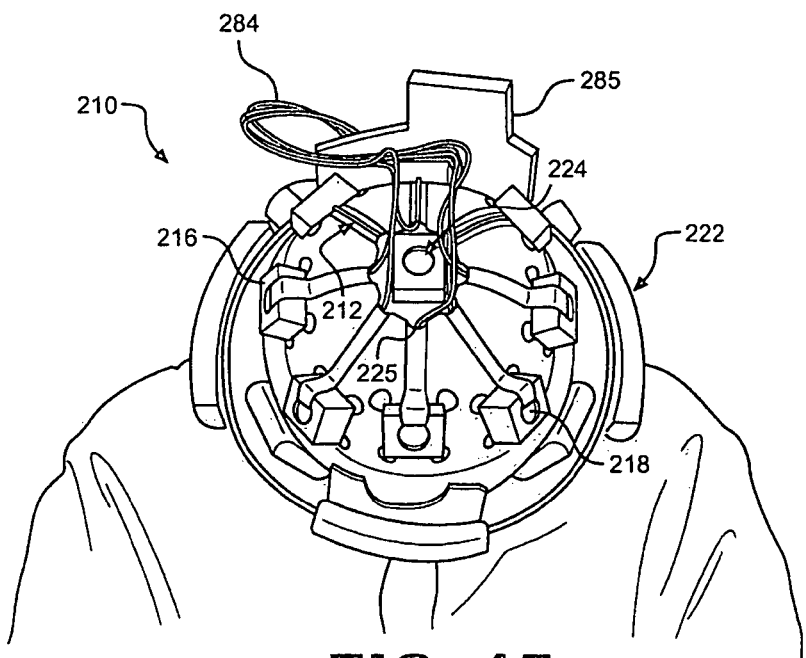
FIG. 15 is a top view of the mounting apparatus of FIG. 13.

The advantages of the present invention lend itself to a variety of applications. In an alternative embodiment of the present invention depicted in FIGS. 13-15 for example, a mounting apparatus 210 is adapted to be incorporated into a helmet, such as a military helmet (not shown). Similar to the second embodiment, mounting apparatus 210 includes eight non-elastic inextensible elements or arms 212 and biasing elements in the form of spring assemblies (not shown), which bias arms 212 towards a subject's head. A plurality of mounting units 216 are connected to arms 212 and are adapted to house objects such as impact sensors 218. Principle elements of mounting apparatus 210 include a circumferential band 222 that fits around the widest part of a subject's head, and a petal element or central mount 224 that sits on top of the head. Like arms 112, arms 212 are rigid, and are attached to central mount 224 via rotating joints 225. In use, arms 212 are biased against a subject's head via springs assemblies built into central mount 224. Spring assemblies can incorporate rigid stops (not shown) so that arms 212 are limited in their maximum rotation with respect to central mount 224 in order to facilitate placement of mounting apparatus 210 on a subject's head.

As with the other embodiments, circumferential band 222 preferably includes one or more adjustment mechanism (not shown). When mounting apparatus 210 is positioned on a subject's head as shown, spring assemblies bias mounting units 216 and associated sensors 218 against a subject's head, providing an upward force against the subject. In order to counter this force, a retaining member in the form of a chin strap assembly 246 is provided. A plurality of communication and power wires 284 connect sensors 218 to a control apparatus and battery source indicated at 285 in a manner similar to that discussed above. Preferably, control apparatus and battery source 285 includes a filter/digitizer unit and a wireless link in order to transfer data from mounting apparatus 210 to a remote location.

It should be recognized that mounting apparatuses 10, 110 and 210 have a wide range of applications and can be utilized, for example, to measure cognitive states of an operator of critical equipment, to record patient data for use in diagnosing an illness such as epilepsy, or to monitor a subject's environment remotely. Although described with reference to use with electrodes 18, 118 and 218, the present invention can be utilized without sensors in order to accurately identify specific positions on a subject's head. For example, a head positioning system may utilize optical detection methods in conjunction with mounting apparatuses 10 and 110 in order to define specific points on a subject's scalp.

Although described with reference to preferred embodiments of the invention, it should be readily understood that various changes and/or modifications can be made to the invention without departing from the spirit thereof. For instance, although shown in the context of positioning EEG sensors in accordance with the international 10/20 electrode configuration, it should be understood that the present invention can be utilized for other desirable object configurations. Additionally, with respect to the first embodiment of the present invention, it should be understood that, although shown as elastic cords, the biasing elements can be in the form of springs or the like. In general, the invention is only intended to be limited by the scope of the following claims.

We claim:

1. A self-locating mounting apparatus in the form of automatically adjustable headgear for accurately positioning objects against a head of a subject, the mounting apparatus comprising:
    a central mount including a plurality of inelastic elements extending therefrom, the central mount being adapted to rest on the top of a subject's head;
    an circumferential band adapted to extend around a subject's head, the circumferential band including an adjustment mechanism;
    a plurality of side elements interconnecting the central mount and the circumferential band;
    a plurality of sliding joints interposed between the central mount and the circumferential band, with the plurality of sliding joints permitting extension and retraction of the central mount relative to the circumferential band;
    a plurality of mounting units attached to the plurality of inelastic elements of the central mount with the plurality of inelastic elements resisting rotation of the plurality of mounting units, wherein each of the plurality of mounting units is adapted to retain an object for positioning against a subject's head; and
    at least one biasing element providing a force biasing the plurality of mounting units against a subject's head.

2. The mounting apparatus of claim 1, further comprising a retaining member adapted to hold the mounting apparatus against a subject's head.

3. The mounting apparatus of claim 2, wherein the retaining member is in the form of an adjustable chin strap assembly.

4. The mounting apparatus of claim 2, wherein the retaining member is in the form of first and second retaining arms each adapted to be positioned behind an ear on a subject's head in order to provide a downward force to the mounting apparatus.

5. The mounting apparatus of claim 1, wherein the mounting apparatus is adapted to hold objects in the plurality of mounting units within approximately ±5 mm of a desired measurement position over a range of subject head sizes.

6. The mounting apparatus of claim 1, wherein the adjustment mechanism of the circumferential band comprises a plurality of segments and interconnecting sliding joints adapted to allow one dimensional extension and retraction parallel to longitudinal axes of the plurality of segments while resisting rotation away from the longitudinal axes.

7. The mounting apparatus of claim 1, wherein the inelastic elements of the central mount hold the plurality of mounting units attached thereto at fixed relative angles.

8. The mounting apparatus of claim 1, wherein each the plurality of sliding joints have an extension or retraction range of approximately ±1.0 cm.

9. The mounting apparatus of claim 1, further comprising objects in the plurality of mounting units, wherein the objects constitute sensors.

10. The mounting apparatus of claim 9, wherein the sensors constitute electroencephalography sensors.

11. The mounting apparatus of claim 9, wherein the sensors constitute impact sensors.

12. The mounting apparatus of claim 1, wherein the mounting apparatus is configured to position the objects against a subject's head in accordance with an international 10/20 electrode placement scheme.

13. The mounting apparatus of claim 1, further comprising releasable means for centering the objects within respective ones of the plurality of mounting units, and releasing the objects once the mounting apparatus is correctly positioned on a subject's head.

14. The mounting apparatus of claim 13, wherein the releasable means comprises tensioning cables.

15. The mounting apparatus of claim 1, wherein the plurality of inelastic elements are in the form of flexible plastic bands.

16. The mounting apparatus of claim 1, wherein each of the plurality of mounting units includes a spring for biasing the object mounted therein against a subject's head.

17. The mounting apparatus of claim 1, wherein the at least one biasing element constitutes at least one elastic cord connected to the plurality of mounting units and providing a retraction force to the plurality of sliding joints to draw the mounting apparatus against a subject's head.

18. The mounting apparatus of claim 17, wherein each of the plurality of mounting units includes a guide through which the at least one elastic cord is threaded.

19. The mounting apparatus of claim 1, wherein the inelastic elements are in the form of rigid arms.

20. The mounting apparatus of claim 19, wherein each rigid arm includes a telescoping mechanism allowing the rigid arm to expand or contract a predetermined amount such that the plurality of mounting units can follow the natural movements of a subject's scalp.

21. The mounting apparatus of claim 20, wherein the rigid arms are connected to the central mount by rotating joints and the biasing elements are in the form of spring assemblies biasing the rigid arms towards a subject's head.

22. The mounting apparatus of claim 21, wherein the rotating joints allow a predetermined finite rotation of the rigid arms with respect to the central mount.

23. The mounting apparatus of claim 1, further comprising additional mounting units each connected to the central mount through respective ones of the plurality of inelastic elements and connected to the circumferential band through the at least one biasing element.

24. The mounting apparatus of claim 23, wherein the additional mounting units are directly connected to the circumferential band through the at least one biasing element.

25. The mounting apparatus of claim 23, comprising further mounting units provided at spaced locations along the circumferential band.

* * * * *